United States Patent [19]

Wendt et al.

[11] 4,001,214

[45] * Jan. 4, 1977

[54] AMINOALKYL ETHERS OF 2,2'- AND 3,3'-DIHYDROXYBENZIL

[75] Inventors: Gerhard R. Wendt, Havertown; Michael W. Winkley, Malvern, both of Pa.

[73] Assignee: American Home Products Corporation, New York, N.Y.

[ * ] Notice: The portion of the term of this patent subsequent to Jan. 27, 1993, has been disclaimed.

[22] Filed: Oct. 30, 1975

[21] Appl. No.: 627,486

[52] U.S. Cl. ............... 260/239 B; 260/239 BF; 424/244; 260/429 R

[51] Int. Cl.$^2$ ........................... C07D 295/08

[58] Field of Search ... 260/239 B, 239 BF, 326.5 J, 260/293.64, 326.5 G

[56] References Cited

UNITED STATES PATENTS

| | | | |
|---|---|---|---|
| 3,207,788 | 9/1965 | Schumann | 260/239 B |
| 3,449,418 | 6/1969 | Werner | 260/239 B |
| 3,935,191 | 12/1975 | Wendt | 260/239 B |

*Primary Examiner*—Alton D. Rollins
*Assistant Examiner*—Mark L. Berch
*Attorney, Agent, or Firm*—David E. Frankhouser

[57] ABSTRACT

Octamethyleneiminoalkyl and heptamethyleneiminoalkyl ethers of 2,2'- and 3,3'-dihydroxybenzil are prepared by reacting the dithallium salt of 2,2'- or 3,3'-dihydroxybenzil with an N-chloroalkyl octamethyleneimine or heptamethyleneimine. The products have antiarrhythmic activity.

3 Claims, No Drawings

AMINOALKYL ETHERS OF 2,2'- AND 3,3'-DIHYDROXYBENZIL

This invention relates to chemical compounds classified in the art of organic chemistry as aminoalkylethers of 2,2'- and 3,3'-dihydroxybenzil having useful pharmacological activity. The compound 5,5'-dichloro-2,2'-bis(2-diethylaminoethoxy)benzil is described by J. Finkelstein and S. M. Linder, *J. Am. Chem. Soc.*, 71, 1010 (1949).

The invention sought to be patented comprises compounds having the molecular formula:

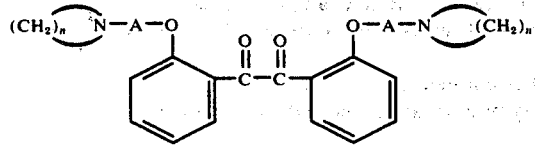

or

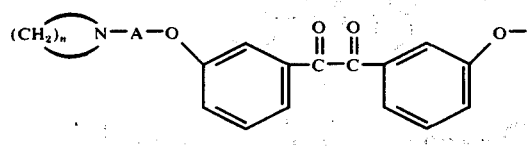

wherein A is a divalent aliphatic hydrocarbon radical of the formula

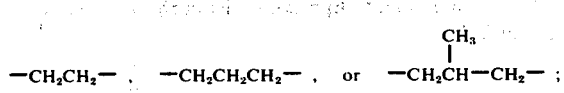

and $n$ is the number 7 or 8; or the non-toxic, pharmaceutically acceptable acid addition salts thereof.

The compounds of Formula I and II in standard pharmacological test procedures elevate the electrical fibrillatory threshold of anesthetized dogs evidencing usefulness as antiarrhythmic agents. In addition, the compounds inhibit ADP-induced blood platelet aggregation indicating usefulness as antithrombitic agents.

The compounds of Formula I or II wherein n is the number 4, 5, or 6 are described in copending application Ser. No. 513,354, now U.S. Pat. No. 3,935,191 filed Oct. 9, 1974.

The compounds of Formula I and II are prepared by condensing a dithallium salt of 2,2'-dihydroxybenzil or 3,3'-dihydroxybenzil with an appropriate N-chloroalkyl octamethyleneimine or N-chloroalkyl heptamethyleneimine in refluxing toluene or toluene-dimethylformamide. The compounds obtained in the free base form can be conveniently isolated and purified in the form of an acid addition salt. Such salts are made by conventional methods such as by combining the base and a suitable acid in a reaction-inert organic solvent.

The dithallium salts are prepared by reaction of 2,2'- or 3,3'-dihydroxybenzil with thallium (I) ethoxide in an inert organic solvent, for example, benzene, toluene, or ethanol-benzene. The salt precipitates from the reaction medium and can be isolated by filtration. [See Taylor et al., *J. Am. Chem. Soc.*, 90, 245 (1968) and Paquet et al., *Can. J. Chem.*, 51, 3855 (1973)].

It is apparent that the compounds of Formula I and II are symmetrically substituted, i.e. the same A—R group is substituted at the oxygens attached to the phenyl moieties of benzil.

For pharmacological purposes the compounds can be employed in the form of acid addition salts with non-toxic and pharmaceutically acceptable acids. Such acids will be apparent to one skilled in the art. Appropriate salts are those formed from either inorganic or organic acids, for example, hydrochloric, hydrobromic, sulfuric, phosphoric, nitric, maleic, fumaric, benzoic, ascorbic, pamoic, succinic, methanesulfonic, acetic, propionic, tartaric, citric, lactic, malic, mandelic, cinnamic, palmitic, itaconic, benzenesulfonic, p-toluenesulfonic, and 2-naphthalenesulfonic.

The methods of making and using the compounds of the invention are illustrated in the following examples:

EXAMPLE 1

2,2'-Bis(Heptamethyleneiminoethoxy)Benzil

To a stirred dry suspension of 2,2'-dihydroxybenzil dithallium salt (30 g.) in toluene (1 liter) was added dropwise 150 ml. of a solution of N-(2-chloroethyl)-heptamethyleneimine (126 g.) in toluene (1 liter). After the mixture had been stirred and heated under reflux for 1 hour, a further 50 ml. of the reagent solution was added and stirring and heating were then continued for a further 4 hours. After cooling, the precipitate was collected by filtration and washed with toluene. The filtrate and washings were evaporated to a syrup which was evaporated further under oil pump vacuum. The residue was dissolved in chloroform and the solution was added to the top of a column (5.3 × 60 cm.) of alumina (Woelm dry-column grade) prepacked in chloroform. The column was eluted with chloroform. Fractions which were homogeneous by TLC on "A10X-25 UV 254" plates with ethyl acetate as developer were evaporated to a syrup which was crystallized by refrigeration at 5°. The crystals were stirred with heptane to yield 17.92 g. of crude base, m.p. 53°–55°. Recrystallization from benzene-heptane gave pure product having the same m.p.

Analysis for: $C_{32}H_{44}N_2O_4$. Calculated: C, 73.81; H, 8.52; N, 5.38 %. Found: C, 73.65; H, 8.41; N, 5.49.

The product as also converted into a bis(citrate) salt. To a warm solution of the free base (7.8 g.) in methanol (100 ml.) was added citric acid (7.5 g.) and the resulting solution was evaporated to smaller volume. Two crystallizations from methanol-ether gave 11.8 g. of product, m.p. 123°–126°.

Analysis for: $C_{44}H_{60}N_2O_{18}$. Calculated: C, 58.40; H, 6.68; N, 3.10 %. Found: C, 57.96; H, 6.63; N, 3.08.

EXAMPLE 2

2,2'-Bis(Octamethyleneiminoethoxy)Benzil

To a stirred dry suspension of 2,2'-dihydroxybenzil dithallium salt (25 g.) in toluene (1 liter) was added dropwise 170 ml. of a solution of N-(2-chloro-ethyl)-octamethyleneimine (53 g.) in toluene (500 ml.). After the mixture had been stirred and heated under reflux for 6 hours, a further 100 ml. of the reagent solution and 200 ml. of N,N-dimethylformamide were added and stirring and heating were then continued for a further 3 hours. After cooling the precipitate was collected by filtration and washed with toluene. The filtrate and washings were evaporated to a syrup which was evaporated further under oil pump vacuum. The residue was dissolved in benzene and the solution was added to the top of a column (5.3 × 54 cm.) of alumina (Woelm dry column grade) prepacked in benzene. The column was eluted with benzene. Fractions which were homogenous by TLC on "A10X-25 UV 254" plates with chloroform-ethyl acetate (7:3) as developer were evaporated to a syrup which crystallized on standing at room temperature. Trituration with heptane gave 17.27 g. of crude free base, m.p. 74°–77°. Recrystallization from chloroform-heptane gave purer product (m.p. 77°–79°) which was characterized as a citrate salt.

To 14.0 g. of the free base in warm methanol (150 ml.) was added 10.5 g. of citric acid. To the resulting solution was added ether. The resulting product was crystallized from methanol to give 18.26 g. of crude citrate salt, m.p. 118°–121°. Two further crystallizations gave 13.45 g. of monocitrate salt, m.p. 119°–122°.

Analysis for: $C_{40}H_{56}O_{11}$ 0.5 $H_2O$. Calculated: C, 64.07; H, 7.66; N, 3.74; $H_2O$, 1.20. Found: C, 63.62; H, 7.95; N, 3.59; $H_2O$, 0.49.

EXAMPLE 3

The antiarrhythmic activity of the compounds of the invention is demonstrated and elicited by the following test method:

The heart of an anesthetized dog is exposed by a left thoractomy. Bipolar electrodes are sutured to the epicardial surface of the left ventricle. The heart is stimulated with square wave pulses of 3 msec. duration and frequency of 60 Hz. for periods of 5 sec. Voltage is increased until fibrillation ensues. The heart is then defibrillated by DC countershock and the procedure repeated at 10 min. intervals. Drugs are administered i.v. over periods of 3 min. and fibrillatory threshold examined 10 min. after start of injection of each dose. Effective antiarrhythmic agents elevate the fibrillatory threshold.

When tested as set forth above the compounds described in the preceding examples elevate the electrical fibrillatory threshold at a dose of 20 mg/kg. body weight.

What is claimed is:

1. A symmetrical compound of the formula:

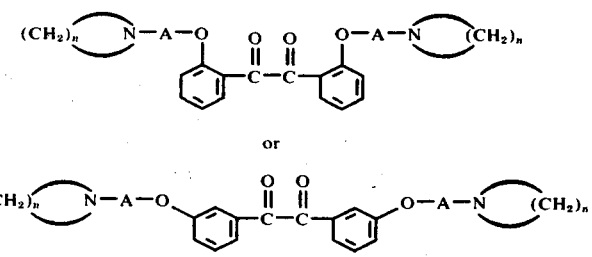

or

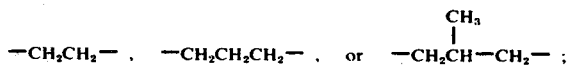

wherein A is a divalent aliphatic hydrocarbon radical of the formula $$-CH_2CH_2-, \quad -CH_2CH_2CH_2-, \quad \text{or} \quad -CH_2\overset{\overset{CH_3}{|}}{C}H-CH_2-;$$

and n is the number 7 or 8; or the non-toxic, pharmaceutically acceptable acid addition salts thereof.

2. A compound accoding to claim 1 which is 2,2'-bis-(octamethyleneiminoethoxy)benzil.

3. A compound according to claim 1 which is 2,2'-bis-(heptamethyleneiminoethoxy)benzil.

* * * * *